US00PP14865P2

(12) United States Plant Patent
Bourne

(10) Patent No.: US PP14,865 P2
(45) Date of Patent: Jun. 8, 2004

(54) GRAPEVINE PLANT NAMED '15-97-77'

(50) Latin Name: *Vitis vinfera*
Varietal Denomination: 15-97-77

(75) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 100 days.

(21) Appl. No.: 10/295,194

(22) Filed: Nov. 15, 2002

(51) Int. Cl.[7] ..... A01H 5/00
(52) U.S. Cl. ..... Plt./205
(58) Field of Search ..... Plt./205

*Primary Examiner*—Kent Bell
(74) *Attorney, Agent, or Firm*—Jondle & Associates PC

(57) ABSTRACT

This new grape plant named '15-97-77' is distinct because of its unusual shape, very firm texture and very large berry size. Berries of the new cultivar are very responsive to applications of exogenous gibberellic acid, almost doubling in size in comparison to untreated fruit. At full maturity in mid-September, berries are extremely firm and sweet.

2 Drawing Sheets

Genus and species: *Vitis vinifera.*

BACKGROUND AND SUMMARY OF THE INVENTION

The new grape plant named '15-97-77' is of *Vitis vinifera* parentage. It is the result of an effort to produce a late-ripening, black, seedless table grape with fruit characteristics superior to currently available black cultivars 'Fantasy Seedless' (unpanteded) and 'Negrita' (unpatented). The female parent (unnamed) (unpatented) resulted from a series of crosses involving 'Hunisa' (unpatented), 'Emperor' (unpatented), and 'Thompson Seedless' (unpatented). The male parent of the cross is an unnamed (unpatented), seedless grapevine resulting from a series of crosses involving 'Emperor', 'Thompson Seedless', and 'Almeria' (unpatented). The hybridization resulting in '15-97-77' was made near McFarland, Calif. in 1994. Seeds from the cross were collected, stratified, and finally planted in a greenhouse in January of 1995. The seedling population of 60 plants was planted in the field in the spring of 1995 near McFarland, Calif. The new grape plant was selected from this seedling population in 1997. It was then propagated by cuttings and grafting to 'Freedom' (unpatented) rootstock in 1998 near McFarland, Calif. Those resulting plants were stable and typical of the original vine.

The new grape plant named '15-97-77' is quite distinctive and unlike any other table grape available on the market known to me. Its very large berries are obovate and average over 10 g with applications of exogenous gibberellic acid. The large clusters average over 1500 g under standard cultural practices, but are quite loose and amenable to packing for cold storage purposes.

COMPARISON WITH PARENTAL CULTIVARS

The new gape plant is similar to its female parent, but differs by having seedless rather than seeded berries. It differs from its male parent by having berries with black skin rather than white skin.

DESCRIPTION OF THE FIGURES

The accompanying drawings illustrate the following.

DETAILED BOTANICAL DESCRIPTION OF THE INVENTION

Figure 1:
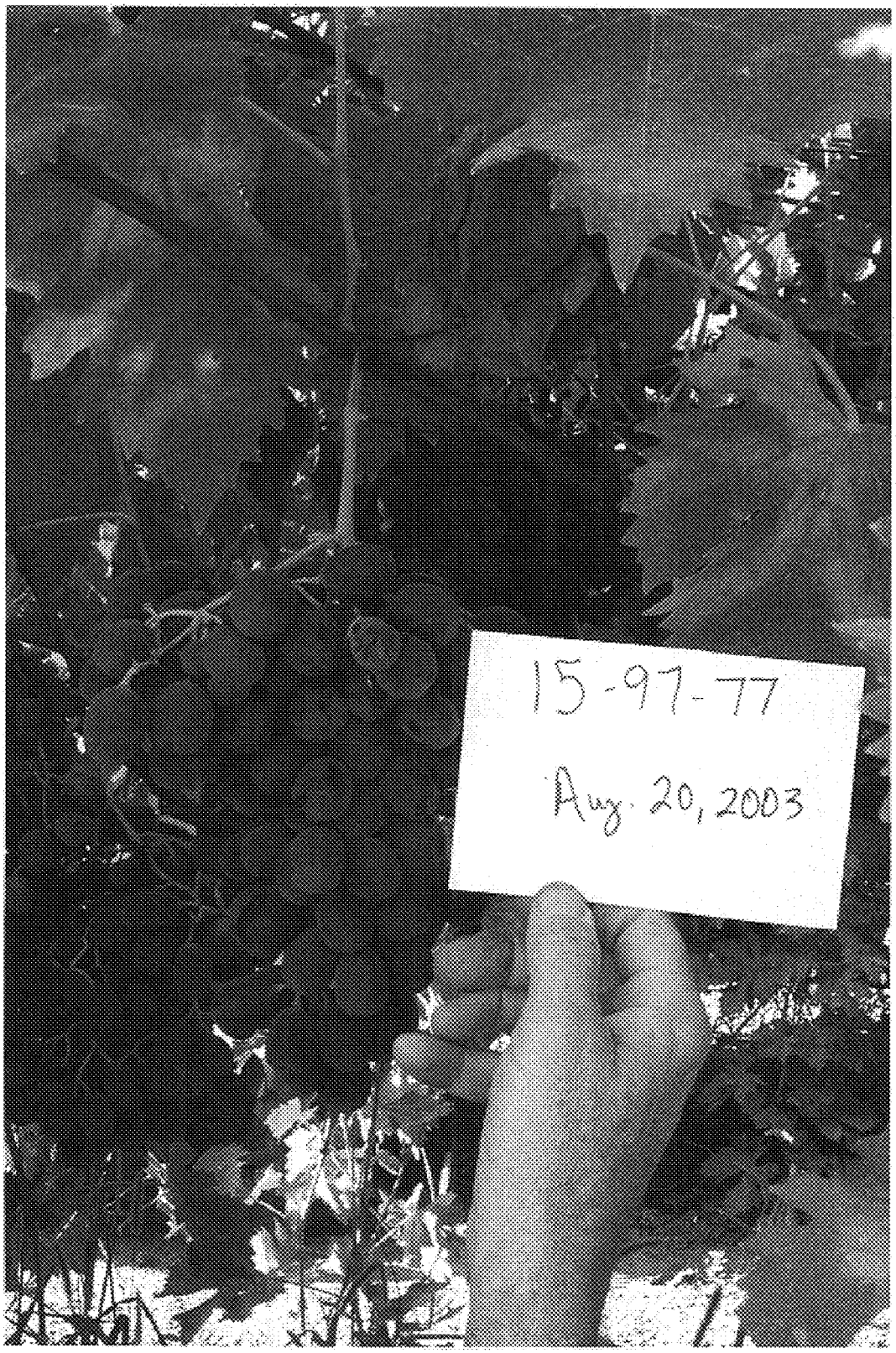
FIG. 1 shows a fruit cluster on the vine.
Figure 2:
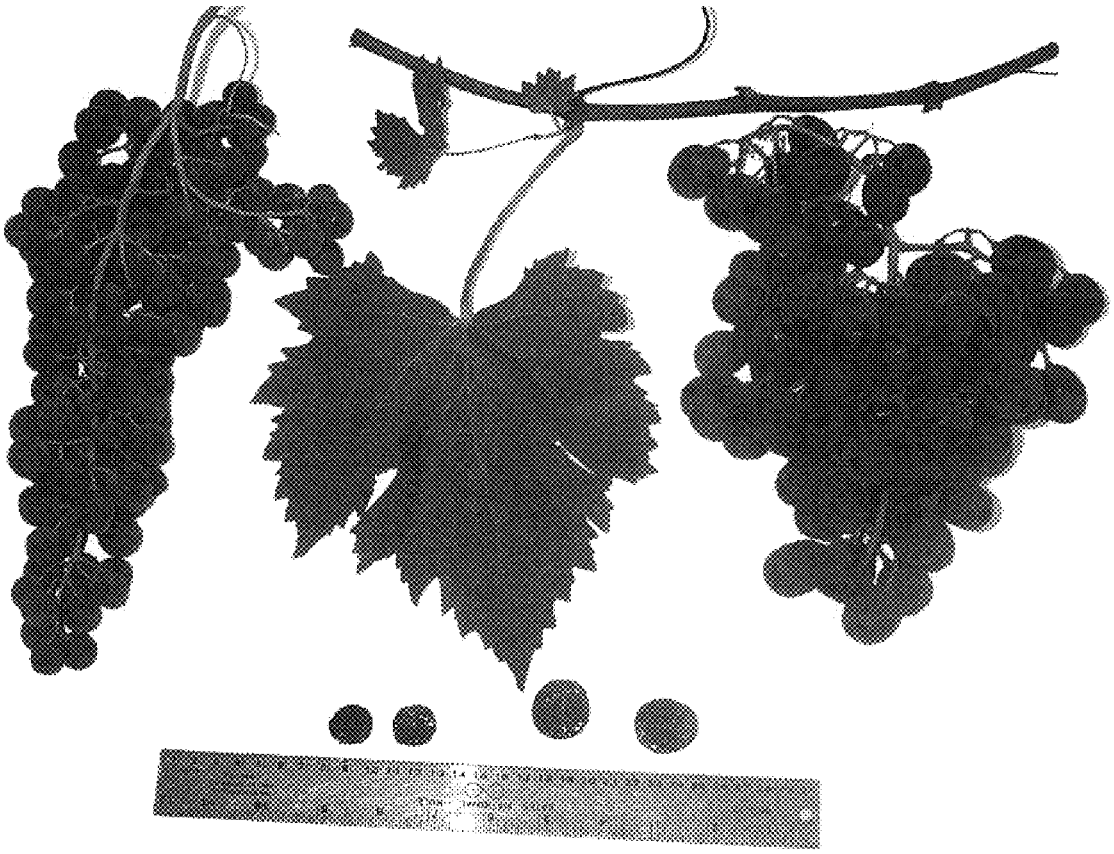
FIG. 2 shows a cane, leaf, natural fruit cluster (left) and fruit cluster following gibberellic acid applications (right).

The following description of grapevine '15-97-77' contains references to color names taken from The Munsell Color Chart for Plant Tissues, published by Munsell Color, New Windsor, N.Y. Descriptors used herein conform to those set forth by the International Board for Plant Genetic Resources Institute Grape Descriptors (Vitis spp.) of 1983 and/or 1997 which were developed in collaboration with the Office International de la Vigne et du Vin (OIV) and the International Union for the Protection of New Varieties of Plants (UPOV) and published in Descriptors for Grapevine (Vitis app.) (Anonymous, International Plant Genetic Resources Institute, 1997, ISBN 92-9043-352-3).

Descriptions of the new invention apply to vines of '15-97-77' grown on 'Freedom' rootstock at a density of 1,537 vines per hectare grown in Kern County, Calif. in 2001. These vines were in their first year of full production having been planted in 1998. These descriptions are believed to apply generally to the new variety grown under similar circumstances elsewhere:

VINE

General:

*Vigor.*—High, vines spur-pruned and shoot thinned to 32 shoots average 291 cm. of growth per cane.
*Density of foliage.*—Moderate.
*Productivity.*—Very productive when spur pruned, up to 70,610 kg./hectare.
*Hardiness.*—Hardiness observed to 0 C.
*Rootstock.*—Freedom.

Trunk:

*Shape.*—Broadly elliptical.
*Straps.*—Long, split.
*Surface texture.*—Shaggy.
*Trunk circumference.*—12.5 cm. at 1 meter height.
*Inner bark color.*—2.5YR 5/6.
*Outer bark color.*—5YR 5/2.

LEAVES

Mature leaves:
*Average blade length.*—16.8 cm.
*Average blade width.*—20.3 cm.
*Size of blade.*—Large.
*Shape.*—Pentagonal.
*Anthocyanin coloration of main veins on the upper side of the blade.*—Absent.
*Mature leaf profile.*—Flat.
*Blistering surface of blade upper surface.*—Absent.
*Leaf blade tip.*—In plane of the leaf.
*Margins.*—Lobed, serrate, undulating.
*Apex.*—Broadly acuminate.
*Bases.*—Sagittate.
*Thickness.*—Medium.
*Undulation of blade between main and lateral veins.*—Slight.
*Shape of teeth.*—Conical, both sides convex.
*Length of teeth.*—5–10 mm.
*Ratio length/width of teeth.*—About 1:1.
*General shape of petiole sinus.*—Variable — open (ovate) to closed.
*Tooth at petiole sinus.*—Absent.
*Petiole sinus limited by veins.*—Absent.
*Shape of upper lateral sinus.*—Closed.
*Prostrate hairs between veins on lower surface of blade.*—Absent.
*Erect hairs between hairs on lower surface of blade.*—Absent.
*Prostrate hairs on main veins on lower surface of blade.*—Absent.
*Density of erect hairs on main veins on lower surface of blade.*—Sparse — hairs distributed along enite length of main veins.
*Prostrate hairs on main veins on upper surface of blade.*—Absent.

Upper surface:
*Summer color.*—7.5 GY 4/4 to 4/6.
*Autumn color.*—5Y 8/6.
*Surface texture.*—Smooth.
*Surface appearance.*—Dull.
*Goffering of blade.*—Absent.

Lower surface:
*Summer color.*—5GY 5/8 to 5/10.
*Autumn color.*—5Y 8/4.
*Anthocyanin coloration of main veins on lower leaf surface.*—Weak.
*Glossiness.*—Low.
*Pubescence.*—Absent.
*Surface texture.*—Smooth.
*Surface appearance.*—Dull.

Petiole:
*Length of petiole.*—15.0 cm.
*Length of petiole compared to middle vein.*—About equal.
*Density of prostrate hairs on petiole.*—Absent.
*Density of erect hairs on petiole.*—Sparse.
*Shape of base of petiole sinus.*—Mostly closed, inside outline is ovate.
*Color.*—In shade: 2.5GY 8/8. In sun: 5R 5/6.

TENDRILS

Number: Bifurcated and trifurcated, forming at all nodes above node 3.
Length: 26.1 cm.
Diameter: 2 mm.
Texture: Smooth.
Color: 5GY 7/10.

WOODY SHOOT

Cane:
*Shape.*—Broadly elliptical.
*Internode length.*—About 11.0 cm.
*Width at node.*—About 1.5 cm.
*Cross section.*—Circular.
*Surface.*—Smooth.
*Main color.*—5YR 5/6.
*Lenticels.*—Inconspicuous.
*Erect hairs on nodes.*—Absent.
*Erect hairs on internodes.*—Absent.

Laterals:
*Shape.*—Broadly elliptical.
*Number.*—Laterals forming at all nodes above node 4.
*Length.*—5.0–129.5 cm.
*Diameter.*—4–9 mm.
*Internode length.*—2–7.5 cm.
*Color.*—2.5YR 4/6.

Buds:
*Shape.*—Slightly pointed.
*Cane bud fruitfulness.*—Basal buds fruitful, 1–2 clusters per shoot.
*Length.*—5 mm.
*Width.*—5 mm.
*Height.*—6 mm.
*Color.*—5YR 4/6 .
*Time of bud burst.*—Mar. 18, 2003.

FLOWERS

General:
*Flower sex.*—Perfect.
*Position of first flowering node.*—Usually the $4^{th}$.
*Number of inflorescences per shoot.*—1 or 2.
*Calyptra color.*—5GY 7/8.
*Ovary length.*—2 mm.
*Ovary width.*—1.5 mm.
*Ovary color.*—5GY 4/8.
*Filament length.*—2 mm.
*Filament color.*—2.5GY 8/2.
*Anther length.*—1 mm.
*Anther color.*—2.5GY 8/8.
*Date of full bloom.*—May 8, 2001 in McFarland, Calif.

FRUIT

General:
*Ripening period.*—Late, about 1 month after 'Thompson Seedless' at Delano, Calif.
*Date of ripening.*—About Sep. 1, 2001.
*Use.*—Fresh market.
*Keeping quality.*—Very good.
*Resistance.*—Insects: typical of *Vitis vinifera*. Diseases: typical of *Vitis vinifera*.
*Shipping quality.*—Good.
*Date of first harvest.*—Sep. 1, 2001.
*Solids-sugar.*—High, about 20 brix at full maturity.
*Refractometer test.*—23.0 brix.

Cluster:
*Bunch size.*—Large.
*Bunch length* (*peduncle excluded*).—About 34 cm.
*Bunch width.*—About 10 cm.
*Bunch weight* (*natural*).—1,046 g.

*Bunch weight* (*gibberellic acid treated*).—1,533 g.
*Bunch density.*—Well-filled, but loose.
*Number of berries.*—172.
*Form.*—Elliptic.

Peduncle:
*Length of peduncle.*—About 10 cm.
*Lignification of peduncle.*—Medium.
*Color.*—5YR 5/6.

Berry:
*Size.*—Large.
*Uniformity of size.*—Uniform.
*Berry weight* (*natural*).—5.6 g.
*Berry weight* (*gibberellic acid treated*).—10.9 g.
*Shape.*—Natural: round; Gibberellic acid treated: obovate.
*Presence of seeds.*—Seedless; most berries develop 1 or 2 small, soft rudimentary seeds less than 1 mm in length. Seeds are dark red, 5R 5/8.
*Cross section.*—Circular.
*Dimensions.*—Longitudinal axis about 1.5 cm.; horizontal axis about 2.3 cm.
*Skin color* (*without bloom*).—5RP 3/2.
*Coloration of flesh.*—Translucent, 2.5GY 8/2.
*Juiciness of flesh.*—Very juicy.
*Berry firmness.*—Very firm.
*Particular flavor.*—Neutral, typical vinifera.
*Bloom* (*cuticular wax*).—Strong.
*Pedicel length.*7–10 mm.
*Berry separation from pedicel.*—Moderate.

Skin:
*Thickness.*—Medium.
*Texture.*—Tender.
*Reticulation.*—Absent.
*Roughness.*—Absent.
*Tenacity.*—Tenacious to flesh.
*Tendency to crack.*—Resistant.
*Particular flavor.*—Skins develop bitter flavor if exposed to sunlight.

What is claimed is:

1. A new and distinct variety of grape plant named '15-97-77' as herein described, illustrated and identified by the characteristics enumerated above.

* * * * *

MZI Selection 15-97-77